(12) United States Patent
Badiali et al.

(10) Patent No.: US 10,197,803 B2
(45) Date of Patent: Feb. 5, 2019

(54) AUGMENTED REALITY GLASSES FOR MEDICAL APPLICATIONS AND CORRESPONDING AUGMENTED REALITY SYSTEM

(71) Applicants: ALMA MATER STUDIORUM—UNIVERSITA' DI BOLOGNA, Bologna (IT); GLASSUP S.R.L., Modena (IT)

(72) Inventors: Giovanni Badiali, Bologna (IT); Giovanni Tregnaghi, Brescia (IT)

(73) Assignees: ALMA MATER STUDIORUM—UNIVERSITA' DI BOLOGNA, Bologna (IT); GLASSUP S.R.L., Modena (IT)

( * ) Notice: Subject to any disclaimer, the term of this patent is extended or adjusted under 35 U.S.C. 154(b) by 88 days.

(21) Appl. No.: 15/129,750

(22) PCT Filed: Mar. 27, 2015

(86) PCT No.: PCT/IB2015/052272
§ 371 (c)(1),
(2) Date: Sep. 27, 2016

(87) PCT Pub. No.: WO2015/145395
PCT Pub. Date: Oct. 1, 2015

(65) Prior Publication Data
US 2017/0160549 A1     Jun. 8, 2017

(30) Foreign Application Priority Data

Mar. 28, 2014  (IT) .............................. MI2014A0541
Mar. 26, 2015  (IT) .............................. MI2015A0440

(51) Int. Cl.
*G02B 27/01*     (2006.01)
*A61B 5/00*       (2006.01)
(Continued)

(52) U.S. Cl.
CPC ........ *G02B 27/0172* (2013.01); *A61B 5/7445* (2013.01); *A61B 2090/365* (2016.02);
(Continued)

(58) Field of Classification Search
CPC .... G02B 27/01; G02B 27/0172; G02B 27/14; G02B 2027/0174; G02B 2027/0178;
(Continued)

(56) References Cited

U.S. PATENT DOCUMENTS 5,742,264 A  * 4/1998  Inagaki ................ G02B 27/017
                                                                345/7
9,551,872 B1 * 1/2017  Kress .................. G02B 27/0172
(Continued)

FOREIGN PATENT DOCUMENTS

JP    2008018015 A  * 1/2008  ............... A61B 8/00
JP    2008018015 A     1/2008
WO   2011002209 A2    1/2011

OTHER PUBLICATIONS

Orcut, Coming soon: Smart glasses that look like regular spectacles, MIT Technology Review, Jan. 9, 2014 (https://www.technologyreview.com/s/523151/coming-soon-smart-glasses-that-look-like-regular-spectacles/.*

*Primary Examiner* — Maurice L. McDowell, Jr.
*Assistant Examiner* — Donna J. Ricks
(74) *Attorney, Agent, or Firm* — Pearne & Gordon LLP

(57) ABSTRACT

The invention describes augmented reality glasses (1) for medical applications configured to be worn by a user, comprising a frame (15) that supports a glasses lens (2a, 2b), wherein the frame (15) comprises an RGB lighting system comprising RGB-emitting devices (16a, 16b, 16c) configured to emit light beams (B1, B2, B3); first optical systems (17a, 17b, 17c) configured to collimate at least partially said
(Continued)

beams (B1, B2, B3) into collimated beams (B1c; B2c; B3c); wherein the frame (15) further comprises a display (3) configured to be illuminated by the RGB lighting system (16) by means of the collimated beams (B1c; B2c; B3c); to receive first images (I) from a first processing unit (10); to emit the first images (I) as second images (IE1) towards the glasses lens (2a, 2b), wherein the lens (2a, 2b) is configured to reflect the second images (IE1) coming from the display (3) as images projected (IP) towards an internal zone (51) of the glasses corresponding to an eye position zone of the user who is wearing the glasses in a configuration for use of the glasses. The invention moreover describes an augmented reality system for medical applications on a user comprising the augmented reality glasses (1) of the invention, biomedical instrumentation (100) configured to detect biomedical and/or therapeutic and/or diagnostic data of a user and to generate first data (D1) representative of operational parameters (OP_S) associated with the user, transmitting means (101) configured to transmit the first data (D1) to the glasses (1); wherein the glasses (1) comprise a first processing unit (10) equipped with a receiving module (102) configured to receive the first data (D1) comprising the operational parameters (OP_S) associated with the user.

25 Claims, 10 Drawing Sheets

(51) Int. Cl.
*G03B 21/20* (2006.01)
*A61B 90/00* (2016.01)
*A61B 90/50* (2016.01)
*G02B 27/14* (2006.01)
*G06F 3/0354* (2013.01)
*G06F 3/16* (2006.01)

(52) U.S. Cl.
CPC ... *A61B 2090/372* (2016.02); *A61B 2090/502* (2016.02); *G02B 27/14* (2013.01); *G02B 2027/0112* (2013.01); *G02B 2027/0141* (2013.01); *G02B 2027/0174* (2013.01); *G02B 2027/0178* (2013.01); *G03B 21/2033* (2013.01); *G06F 3/03543* (2013.01); *G06F 3/167* (2013.01)

(58) Field of Classification Search
CPC ....... G06F 3/03543; G06F 3/167; A61B 5/00; A61B 5/7445; A61B 2090/502; A61B 2090/372; A61B 2090/365
See application file for complete search history.

(56) References Cited

U.S. PATENT DOCUMENTS

| | | | |
|---|---|---|---|
| 2005/0203380 A1* | 9/2005 | Sauer | G02B 7/002 |
| | | | 600/417 |
| 2009/0231687 A1 | 9/2009 | Yamamoto | |
| 2011/0211260 A1 | 9/2011 | Yamamoto | |
| 2013/0069985 A1* | 3/2013 | Wong | G02B 27/017 |
| | | | 345/633 |
| 2013/0241907 A1* | 9/2013 | Amirparviz | G02B 27/0093 |
| | | | 345/207 |
| 2014/0320547 A1* | 10/2014 | Lee | G09G 3/001 |
| | | | 345/690 |

* cited by examiner

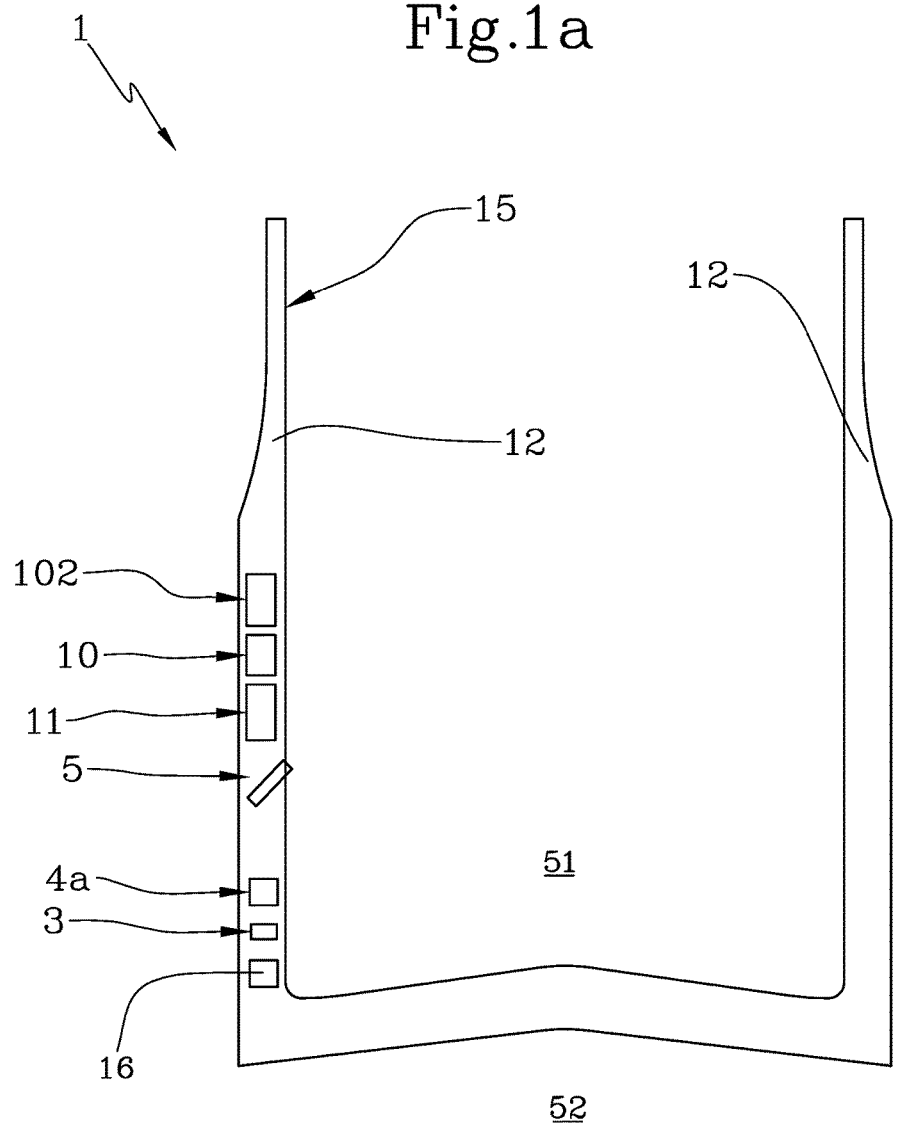

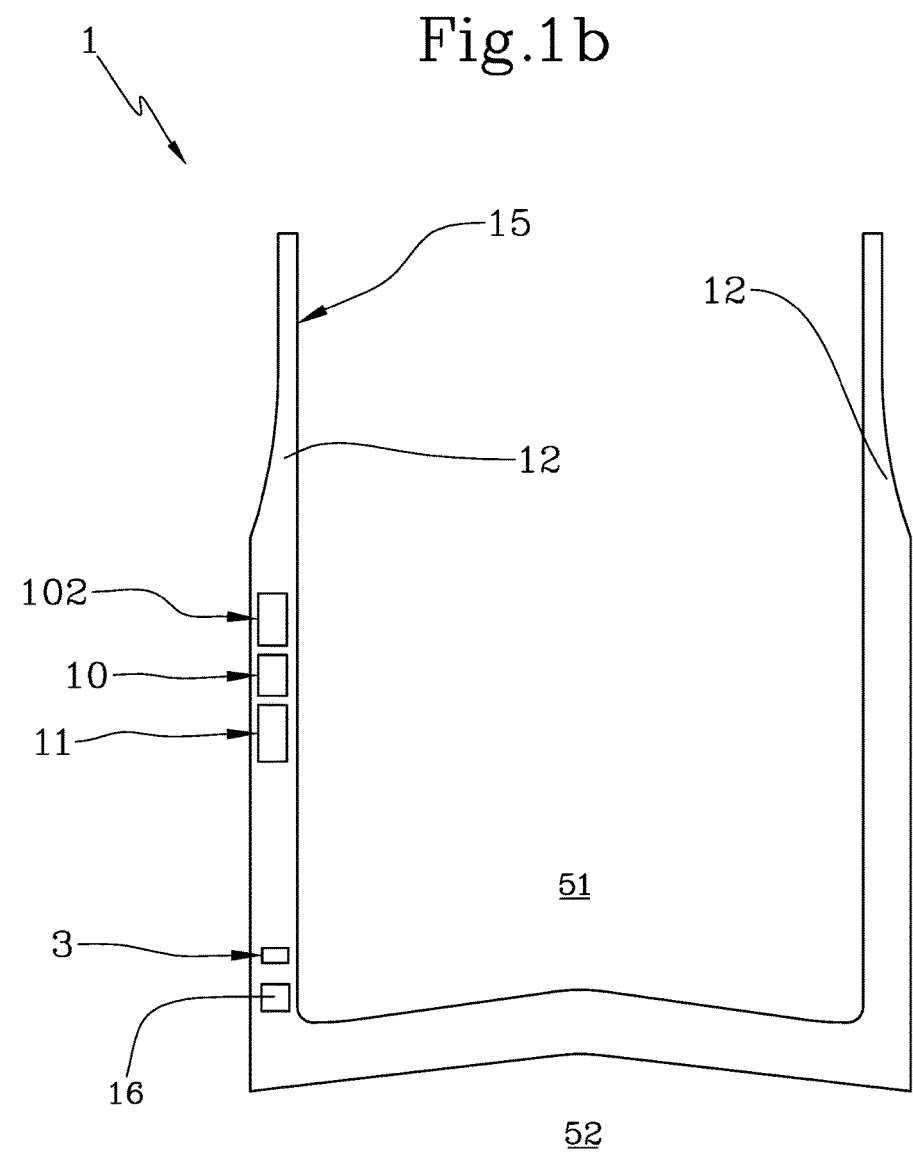

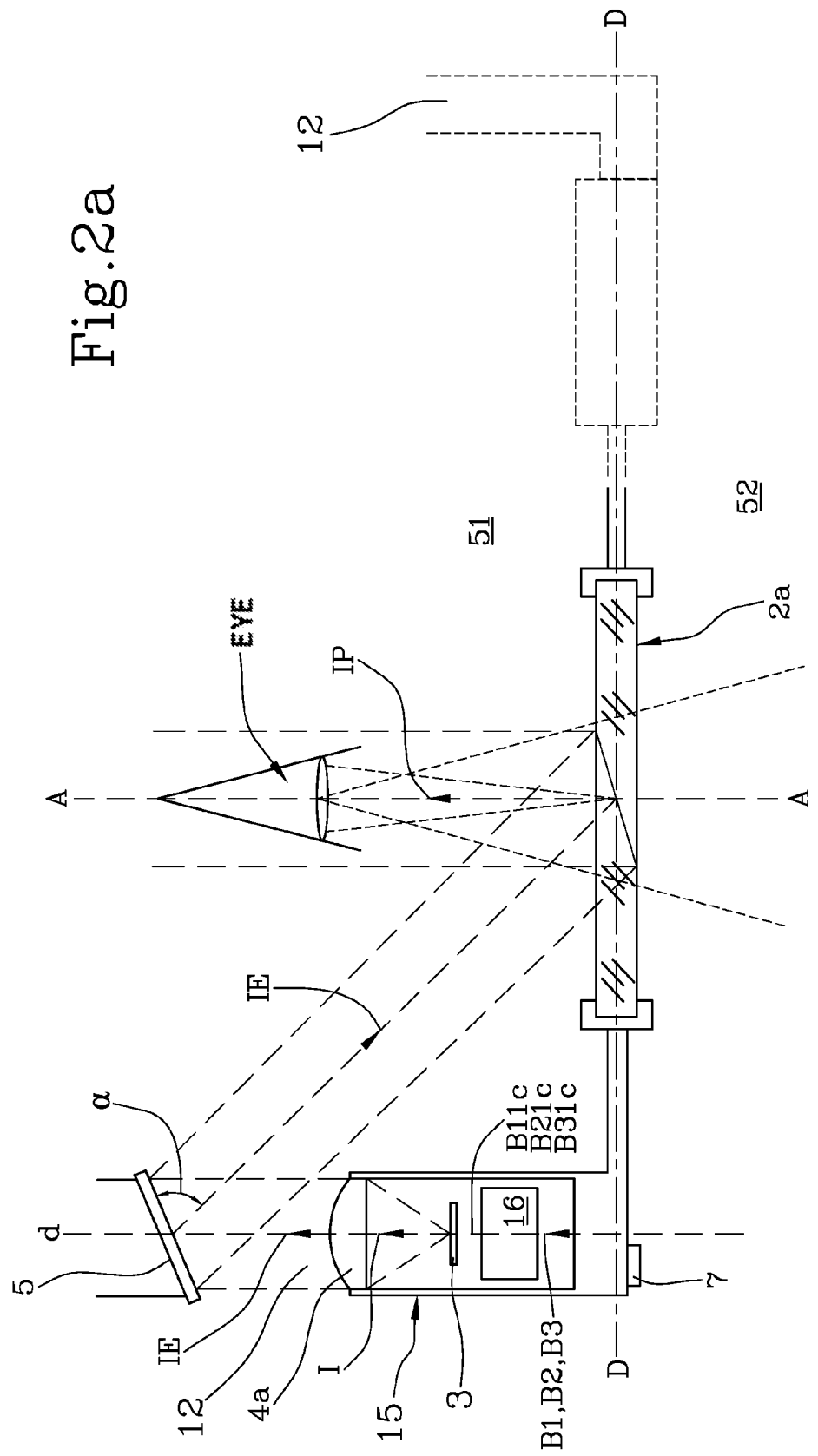

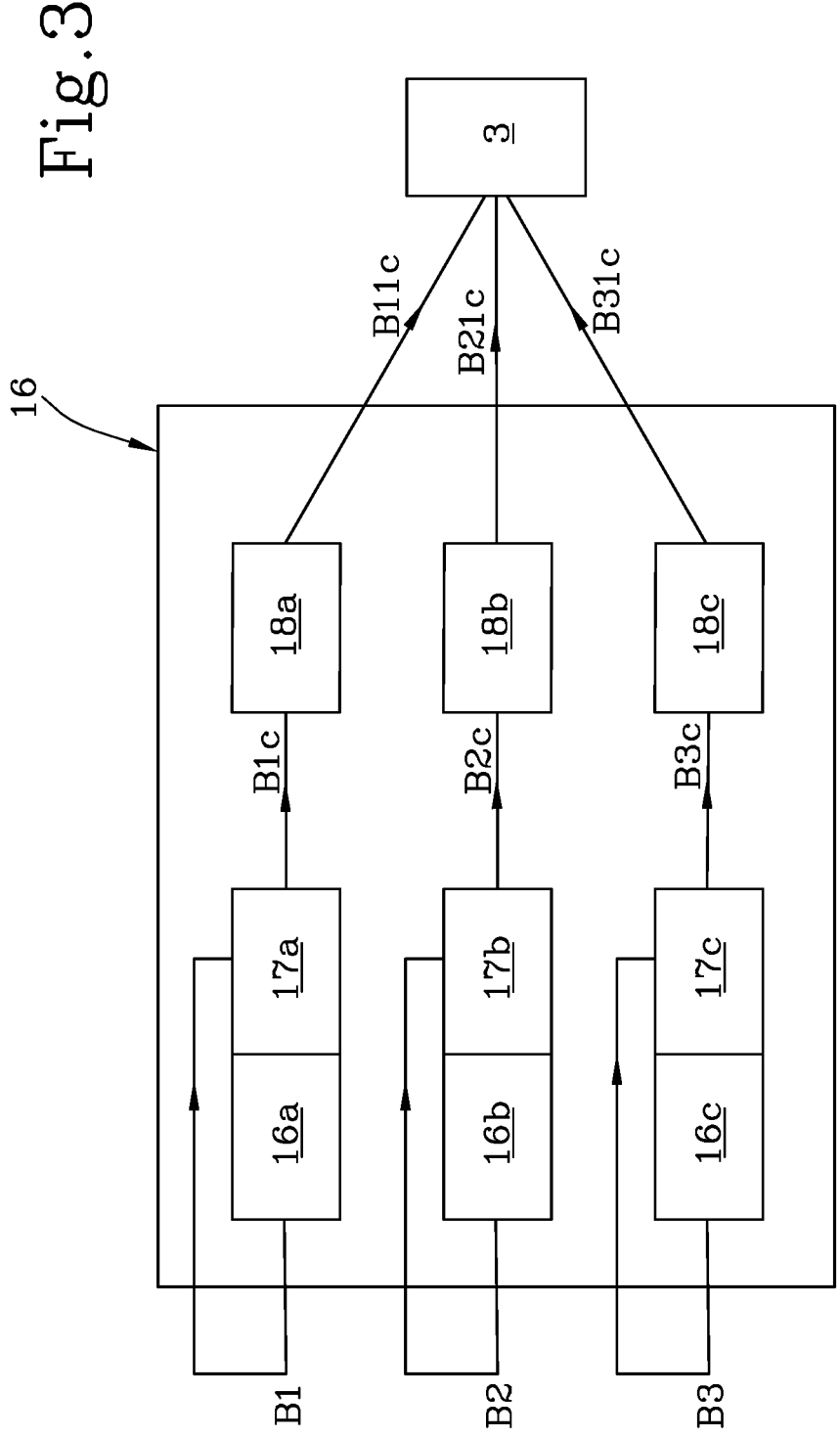

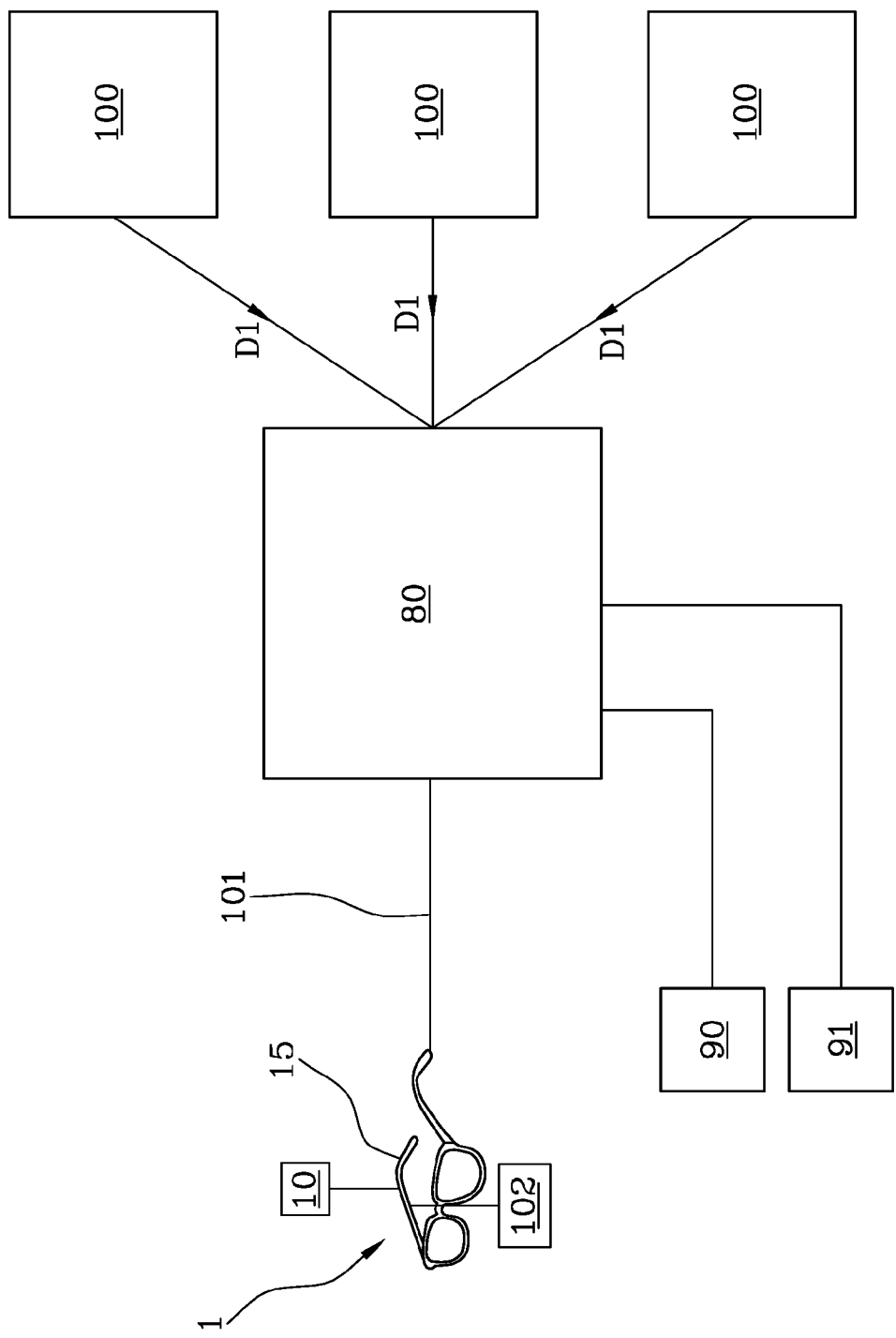

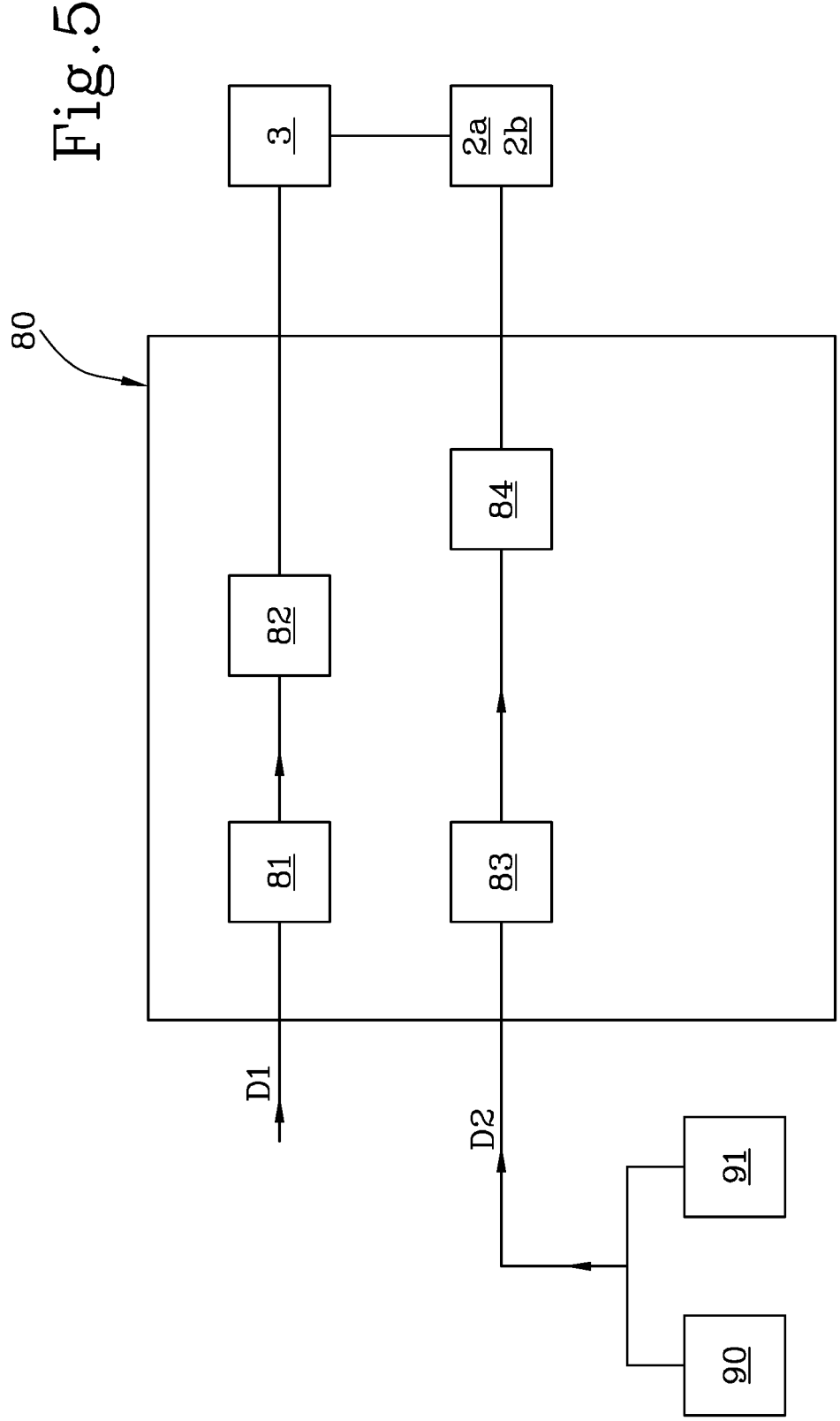

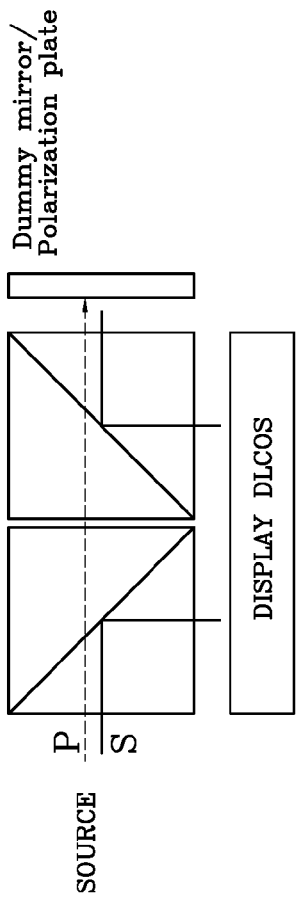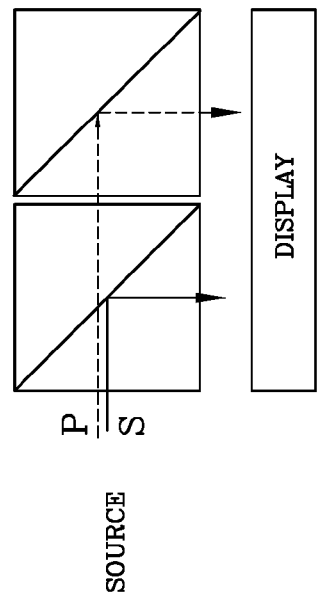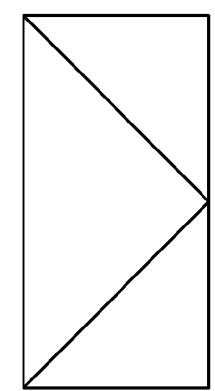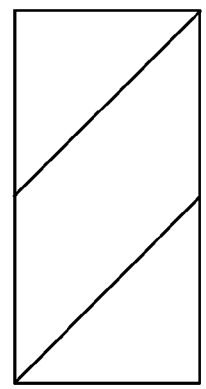

AUGMENTED REALITY GLASSES FOR MEDICAL APPLICATIONS AND CORRESPONDING AUGMENTED REALITY SYSTEM

FIELD OF APPLICATION

The present invention relates to augmented reality glasses for medical applications. The present invention also relates to an augmented reality system for medical applications in which the glasses interface with devices for biomedical applications.

PRIOR ART

The known computerized support systems for surgical interventions provide for some operating room instruments to display on a monitor a digital representation or video of the area of the patients being operated on, to enable the surgeon to have precise topographical and operative information necessary for carrying out the surgery.

Surgeons often shift their visual attention from the operating field, and thus from the anatomical structure being acted upon, to the monitor which displays graphic information to support the surgery.

This represents a risk for the precision of the surgery and great discomfort for the operator; in fact, every surgical act (for example the repositioning of bone segments) requires constant visual monitoring and the standard use of a monitor obliges the surgeon to divert his gaze for the time necessary to check the images on the monitor and simultaneously keep a grip on the instrument such images are acquired by or the instrument being represented in the images (together with the anatomy of the patient) or in some cases the anatomical part operated on.

It is evident that with this operating method part of the increase in precision imparted by the use of the monitor which shows the acquired images is undermined by the interference of the lack of a direct and continuous visual monitoring of the scene of the operation and/or the method makes the entire procedure particularly difficult for the surgeon.

The applicants have perceived that the current approach, though an improvement over traditional techniques not aided by a computer, does not ensure the advantages that the power of the instruments available today could and should have.

The applicants have verified that a different approach determines technical advantages and, consequently, a better success of the surgery, which can be fundamental in the majority of practical cases.

SUMMARY OF THE INVENTION

The object of the present invention is to provide instrumentation, in particular augmented reality glasses, which enable a representation of the operating scene that is free of the above-described defects.

A further object of the present invention is to provide an augmented reality system comprising such glasses which enables the above-described defects to be overcome.

Another object is to provide augmented reality glasses and an augmented reality system that ensure the possibility for medical, paramedic or auxiliary personnel to operate in better conditions of safety and efficiency.

In a first aspect, the present invention relates to augmented reality glasses configured to be worn by a subject, wherein the glasses comprise a frame that supports a glasses lens, wherein the frame comprises:
an RGB lighting system comprising:
  at least one RGB-emitting device configured to emit a light beam;
  at least a first optical system configured to collimate at least partially the beam received from the at least one RGB-emitting device into a collimated beam;
a display configured to
  be illuminated by the RGB lighting system by means of at least the collimated beam;
  receive first images from a first processing unit;
  emit the first images as second images towards the glasses lens;
  wherein the lens is configured to reflect the second images coming from the display as images projected towards an internal zone of the glasses corresponding to an eye position zone of the user who is wearing the glasses in a configuration for use of the glasses.

In a second aspect, the present invention relates to an augmented reality system for medical applications on a user, wherein the system comprises:
  augmented reality glasses of the invention;
  biomedical instrumentation configured to detect biomedical and/or therapeutic and/or diagnostic data of a subject and to generate first data representative of operational parameters associated with said user;
  transmitting means configured to transmit said first data to said glasses;
wherein said glasses comprise a first processing unit equipped with a receiving module configured to receive first data comprising operational parameters associated with said user.

In one or more of the aspects specified above, the present invention can comprise one or more of the following features.

Preferably, it is envisaged that the RGB lighting system in the glasses is one among
  an RGB LED lighting system;
  an RGB laser diode system;
  an RGB white LED system.

Preferably, said frame comprises an optical system configured to:
  receive images from said display;
  process said images so as to create processed images;
  send said processed images towards reflecting elements or towards the lens.

Preferably, the reflecting elements are configured to receive said processed images and reflect them at a first predefined angle towards said glasses lens, so as to project said processed image onto said glasses lens.

Preferably, the display comprises a beam splitter and it is a reflecting element.

Preferably, the lighting system comprises second optical systems configured to filter said collimated light beams into predetermined frequencies, determining three sub-beams and said display is configured to be illuminated by said lighting system by means of at least said sub-beams.

Preferably, the lighting system further comprises two dichroic filters which receive the light beams coming out of second optical systems.

Preferably, the lens is configured to reflect said second images or said processed images with images projected towards an internal zone of the glasses corresponding to an eye position zone of said user who is wearing said glasses, said projected image being projected along the visual axis of the eyes of the user who is wearing said glasses in a configuration for use of the glasses.

Preferably, the lens is realised as a semi-reflective mirror.

Preferably, the lens is realised as a holographic component.

Preferably, said holographic component is monochromatic.

Preferably, said holographic component is polychromatic.

Preferably, the lens is made of nanostructured material and is based on surface plasmonic processes.

Preferably, the augmented reality system for medical applications on a user comprises: augmented reality glasses; biomedical instrumentation configured to detect biomedical and/or therapeutic and/or diagnostic data of a user and to generate first data representative of operational parameters associated with said user;
transmitting means configured to transmit said first data to said glasses;
wherein said glasses comprise a first processing unit equipped with a receiving module configured to receive the first data comprising operational parameters associated with the user Preferably, said operational parameters comprise one or more among diagnostic parameters, clinical parameters in text and/or graphic form, vital parameters, technical parameters related to instrument settings, biological parameters, clinical information concerning the patient and similar data.

Preferably, the augmented reality system further comprises a second processing unit comprising:
a receiving module configured to receive said first data representative of operational parameters;
a display module configured to display said first data on said display in such a manner that the data are projected at the centre of the lens;
a command module configured to receive second data representative of a position on said lens where said first data must be displayed;
a positioning module configured to project said first data on said lens in a given position based on said received second data.

Preferably, the first processing unit comprises said second processing unit.

Preferably, the system comprises a command unit associated with said processing unit, wherein said command unit is configured to generate said second data representative of a position on said lens where said first data must be displayed.

Preferably, the command unit comprises a voice command receiver.

Preferably, the command unit comprises a mouse.

Preferably, the biomedical instrumentation comprises one or more among:
PACS systems (picture archiving and communication system);
surgical navigators;
endoscopes;
integrated operating room systems that collect the patient's vital parameters and the surgical instrument settings;
integrated systems for collecting the patient's clinical data and vital parameters for use outside the operating room;
surgical simulators for educational activities.

Preferably, the transmitting means is configured to transmit said first data to said glasses, in particular to the receiving module of the first processing unit, and comprises a data connector.

Preferably, the transmitting means is configured to transmit said first data to said glasses, in particular to the receiving module of the first processing unit, and comprises a wireless transmitter.

The invention, as described, achieves the following technical effects:
it provides augmented reality glasses and a corresponding system in which the possibility of perception of reality is increased, thus making it possible, in the case of surgical interventions, to access precise image and data content sure to be an aid to the surgery, without diverting attention from the field of action of the aforesaid surgery.

The use of the glasses of the invention in a surgical setting represents a highly innovative application.

This mode in fact enables direct exploitation, in loco, of images normally displayed on external monitors. Such images are displayed in the form of "augmented reality" in the central area of the visual field, thus becoming available, depending on the surgeon's needs, as virtual images that can be superimposed on the image of the external scene, preferably in the area involved in the surgical operation.

Moreover, the embodiments of the invention make it possible to better perceive:
the surrounding scene observed through the glasses;
written and drawn multimedia content such as SMS text messages, e-mails, contact notes, calendar, navigator, data of interest, mechanical and electronic diagrams and other content.

Furthermore, the embodiments of the invention make it possible to:
access real image content such as photographs, videos, Internet and, always depending on the degree of complexity of the model of glasses produced, listen/speak in phone conversations, listen to music and so forth;
carry out several actions simultaneously, thus increasing the possibility of action of the user, for example enabling surgeons to operate without diverting their attention from the action taking place.

The technical effects mentioned and other technical effects will emerge in more detail from the description, given below, of an embodiment shown by way of non-limiting example with reference to the attached drawings.

BRIEF DESCRIPTION OF THE DRAWINGS

FIG. 1a shows an overall view of the augmented reality glasses according to a first embodiment of the invention.

FIG. 1b shows an overall view of the augmented reality glasses according to a second embodiment of the invention.

FIG. 2a shows details of the glasses of FIG. 1a.

FIG. 3 shows details of a component of the glasses of FIGS. 1 and 2.

FIG. 4 shows an augmented reality system comprising the glasses of the preceding figures.

FIG. 5 shows details of a component of FIG. 4.

FIGS. 7 and 8 show details of the components of the glasses of the invention.

DETAILED DESCRIPTION OF THE INVENTION

Figure 2B:
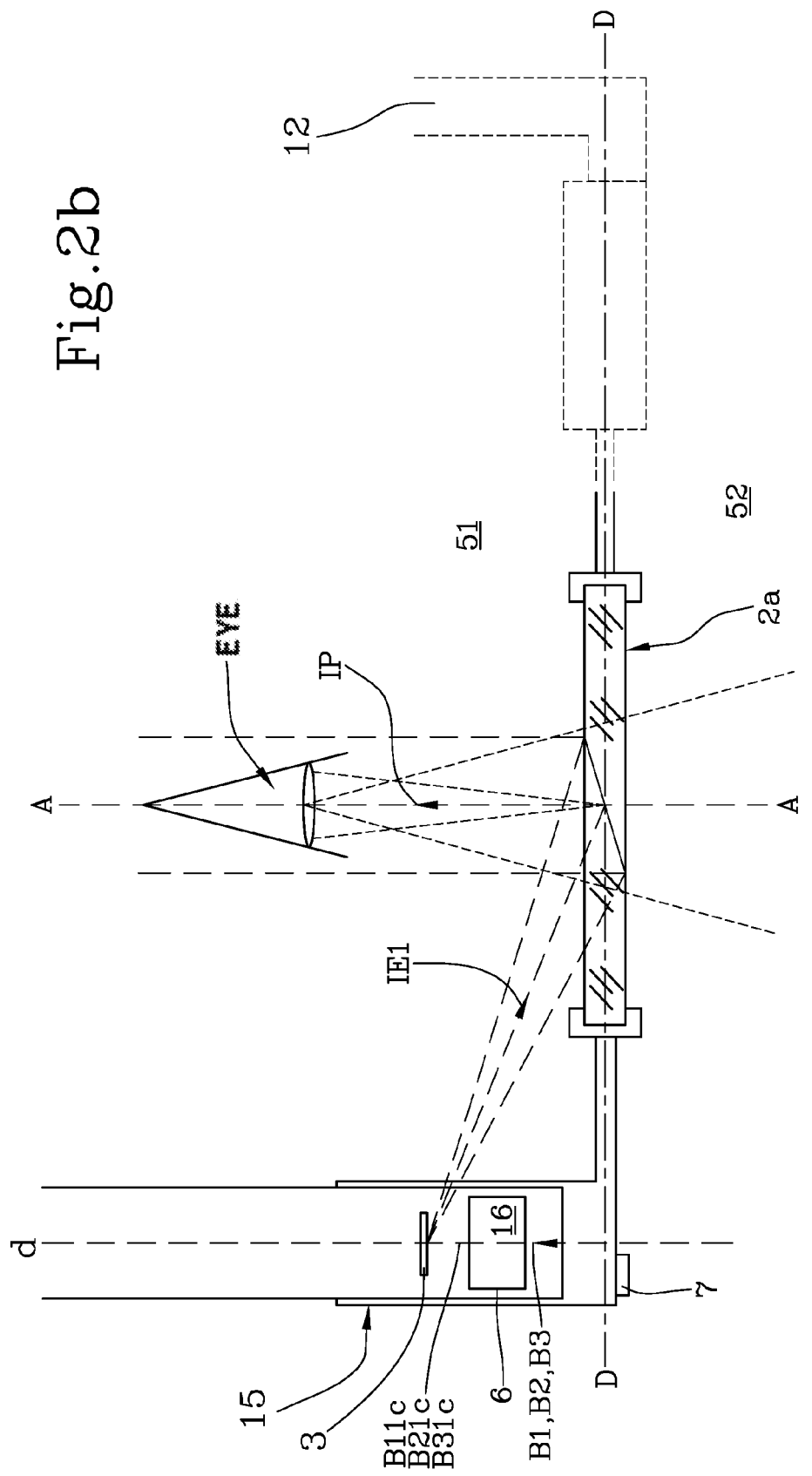
FIG. 2b shows details of the glasses of FIG. 1b.

The augmented reality glasses for medical applications are a device in the form of glasses provided with lenses, capable of projecting, in the visual field of the operator, preferably a health care worker (physician, surgeon, nurse, ambulance service volunteer, etc.) data, information and static or dynamic images of medical relevance (patient data, test results, vital parameters of the patient or other information originating from the instruments being used, X-ray images, X-ray images for navigation, virtual images). The position of the data can be set in any point of the visual field of the operator, that is, where they feel is most useful and comfortable, viewing not being limited to a single peripheral point of the visual field.

With reference to FIG. 1, it shows augmented reality glasses 1 configured to be worn by a user.

Preferably, the image-processing optical structure shown on only one temple of the glasses can be reproduced on both temples to provide a stereoscopic effect.

With particular reference to FIGS. 1a, 1b and 2a and 2b, the augmented reality glasses 1 comprise a frame 15 that supports a glasses lens 2a, 2b.

The frame is completed by two temples 12 supporting the glasses.

The frame 15 divides the space into two zones, a internal zone 51 of the glasses corresponding to an eye position zone of the user who is wearing the glasses in a configuration for use of the glasses, and an external zone 52 represented by the remaining part of space.

According to the invention, the frame 15 has a miniaturised display 3 associated with it, preferably mounted in the frame 15.

Advantageously, according to the invention the frame 15 is associated with an RGB lighting system 16.

The lighting system is configured to illuminate the display 3.

Preferably, the RGB lighting system 16 is a LED lighting system.

Alternatively, the RGB lighting system 16 is a laser diode system.

Alternatively, the RGB lighting system 16 is a white LED system.

Preferably, the frame 15 comprises an RGB LED lighting system 16 and a reflection means 3.

In particular, the reflection means 3 comprises the display 3 configured to emit first images I or second images IE1.

Alternatively, or in addition, the display 3 is configured as a transmitting means.

With particular reference to FIG. 3, the RGB lighting system 16 comprises RGB-emitting devices 16a, 16b, 16c configured to emit light beams B1, B2, B3, preferably unpolarised;

In a preferred embodiment, with reference to FIGS. 2a and 2b and 3 and 6, the lighting system 16 is an RGB LED lighting system and comprises LEDs 16a, 16b, 16c configured to emit respective light beams B1, B2, B3, preferably unpolarised.

As is well known, LEDs (Light-Emitting Diodes) are diodes configured to emit a light beam.

In particular, a LED is an optoelectronic device that exploits the optical properties of several semiconductor materials capable of producing photons via a spontaneous emission phenomenon.

Figure 6:
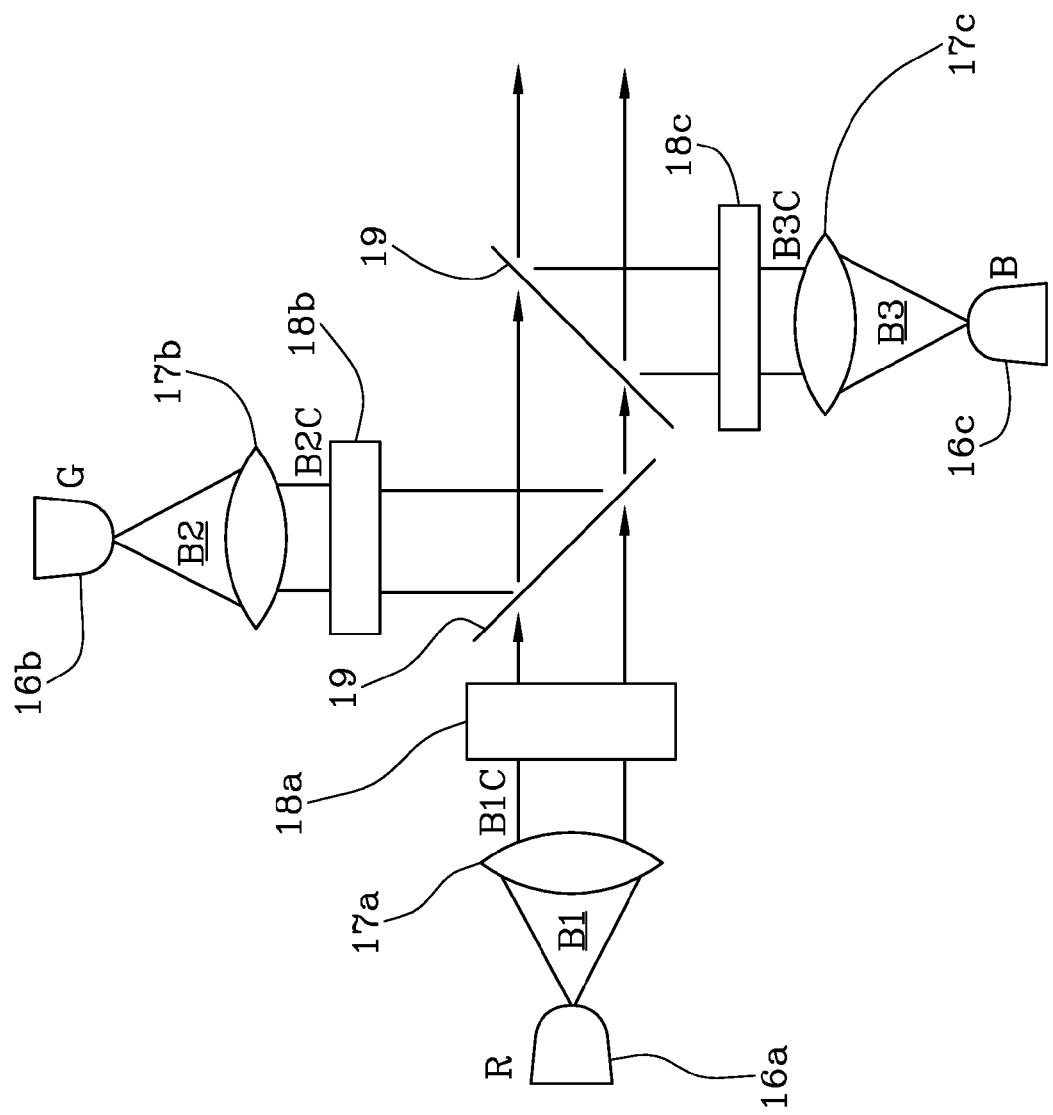
FIG. 6 shows an embodiment of the component of FIG. 3.

Advantageously, according to the invention, as shown in FIG. 6, the RGB LED lighting system 16 is a LED lighting system RGB which comprises the LEDs 16a, 16b, 16c in the red, green and blue frequencies, respectively.

The RGB lighting system 16 further comprises first optical systems 17a, 17b, 17c configured to collimate at least partially the beams B1, B2, B3, preferably unpolarised, received from the RGB-emitting devices 16a, 16b, 16c into collimated beams B1c; B2c; B3c.

In particular, the RGB lighting system 16 comprises the first optical systems 17a, 17b, 17c configured to collimate at least partially the beams coming from the LEDs 16a, 16b, 16c into collimated beams B1c; B2c; B3c.

The RGB lighting system 16 further comprises second optical systems 18a, 18b, 18c configured to filter the collimated light beams B1c, B2c, B3c into predetermined frequencies f1, f2, f3, determining three sub-beams B11c, B21c, B31c, In particular, the second optical systems 18a, 18b, 18c are configured to filter the collimated light beams B1c, B2c, into the frequencies f1, f2, f3 of red, green and blue, respectively, in such a way as to reduce the passband for each individual colour.

In one embodiment of the invention, the second optical systems 18a, 18b, 18c comprise band-pass filters.

In one embodiment, the passband is reduced to values in the order of nanometers.

In particular, FIG. 6 shows an embodiment of the system in which, besides the described elements, there are dichroic filters 19 that receive the light beams coming out of the second optical systems 18a, 18b, 18c.

In particular, FIG. 6 shows an embodiment of the system in which, besides the already described elements, there are filters 19 that receive the light beams coming out of second optical systems 18a, 18b, 18c and cause them to be superimposed and collimated.

Alternatively, the dichroic filters 19 receive the light beams coming out of the first optical systems 17a, 17b, 17c and cause them to be superimposed and collimated.

The white LED system will comprise only one of the previously described optical systems.

In a preferred embodiment, the RGB laser diode lighting system will be analogous to the previously described RGB LED lighting system, but without the second optical systems configured to filter the light beams.

The RGB lighting system 16 is configured to illuminate the display 3.

In other words, the RGB lighting system 16 has enough power to ensure a lighting of the display 3 that is sufficient to superimpose the image of the display 3 on that of the real surrounding scene.

The technical effects achieved by the RGB lighting system 16 in the glasses of the invention are to illuminate the display, maximising the incident light on the display and obtaining an image necessary for the application.

Alternatively, in a case not included in the invention, the lighting system can be monochromatic.

Preferably, the lighting system is a monochromatic LED system.

Preferably, the lighting system is a monochromatic laser diode system.

Preferably, the lighting system is a white LED system.

The glasses 1 according to the invention further comprise a first processing unit 10 configured to process first data D1 input to the glasses 1 to generate corresponding first images I on the display 3.

In particular, the first processing unit 10 is an electronic control, interface and power supply system.

The first processing unit 10 will serve to manage communication with equipment external to the glasses, lighting systems and microdisplays and will comprise an electronic interface between video signals coming from the outside and the display.

In other words, the first processing unit 10 is configured to send images to the display 3. More in general, the first processing unit 10 is configured to perform one or more among the operations of controlling the power supply and/or switching on of the display 3, controlling the switching on of the LEDs or laser diodes of the lighting system and varying the levels of illumination of the LEDs or laser diodes.

The first processing unit 10 according to the invention comprises a receiving module 102 configured to receive as input the first data D1.

In a preferred embodiment of the invention, the first data D1 comprise operational parameters OP_S representative of diagnostic parameters, clinical parameters in text and/or graphic form, vital parameters, technical parameters related to instrument settings, biological parameters, clinical information concerning the patient and similar data.

According to the invention, the reflection means 3, in particular the display 3, are configured to be illuminated by the LED lighting system 16 by means of at least the collimated beams B1c, B2c, B3c.

In a first preferred embodiment of the invention (FIG. 2b), the display 3 is configured to receive first images I from the processing unit 10; the display 3 is further configured to reflect the second images IE1 towards the glasses lens 2a, 2b; in other words, the display 3 is also a reflecting element.

In greater detail, the display 3 can be an LCD, LCoS or DLP display.

In particular, the LCD display is configured as a transmitting means.

Figure 7:
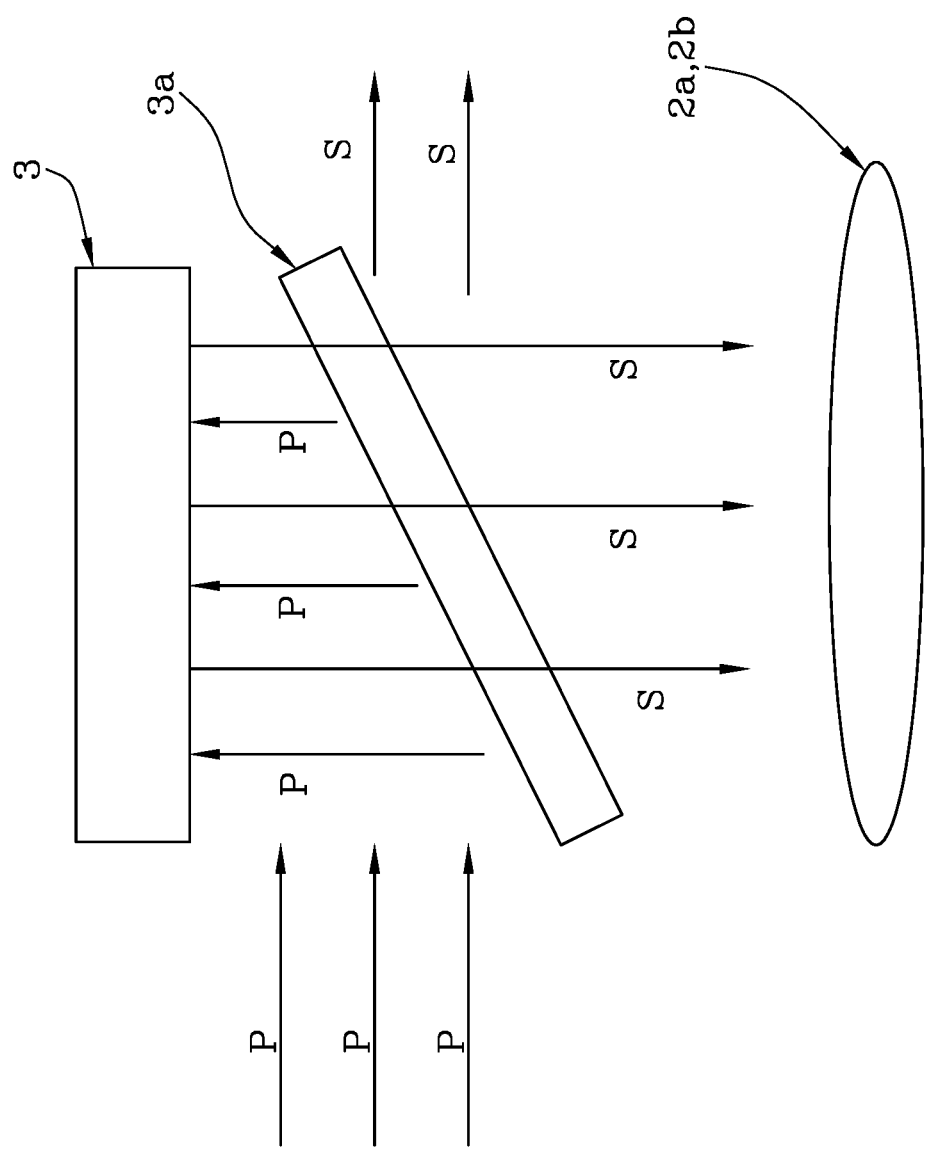

In one embodiment, with reference to FIG. 7, and limited to the case of an LCoS and DLP display, the display 3 comprises a beam splitter 3a configured to send part of the unpolarised light P incident thereupon towards the display 3; in other words, the beam splitter 3a suitably polarises the incident unpolarised light beam P so that the display 3 in turn reflects a polarised light beam S, in the direction of the lens 2a, 2b.

More in general, the display 3, limited to the case of an LCoS and DLP display, comprises a beam splitter 3a configured to select and divert, of the totality of the light incident thereupon, only the polarised part of type P towards the display 3; in other words, the beam splitter 3a suitably separates the polarisation components of the incident beam, according to the polarisation components thereof, S and P, into two polarised beams respectively of type P on the one hand (sent towards the display 3) and of type S on the other (sent towards the lens (2a,2b)), so that the display 3 in turn reflects a beam of polarised light S in the direction of the lens 2a, 2b.

In one embodiment of the invention, with reference to FIGS. 8a and 8b, the beam splitter 3a can be a double beam splitter realised according to the configuration shown in FIGS. 8a1, 8a2.

If the beam splitting cubes were united in the configurations of FIG. 8a, this would considerably reduce the risk of light scattered by the contact surfaces, which would give rise to a non-uniform luminous line at the centre of the projected image.

The advantages of such solutions are considerable and in particular:
- 81% efficiency instead of 40%;
- Glass thickness limited to less than 5 mm (instead of 10 mm) and negligible or minor focus drift;
- Reduction of the optical path between LED and display by a factor of 2 and further gain in brightness.

In particular, FIG. 8b shows the display/double beam splitter configuration deemed advantageous.

The use of a double polarised beam splitter can make it possible to exploit 50% of the light that would otherwise be lost due to the selection of only one polarisation. The critical point is the junction between the two beam splitters, which must not scatter (render grainy) the light, making it visible as a luminous line at the centre of the display. FIG. 8b shows two possible solutions with mutually identical beam splitters (FIG. 8b1) and two beam splitters, one of which reflects the component S and the other the component P (FIG. 8b2). The lens 2a, 2b is configured in turn to reflect the second images IE1 originating from the display 3 as an image IP projected towards the internal zone 51 of the glasses 1.

In a second preferred embodiment of the invention (FIG. 2a), the frame 15 comprises an optical system 4a,4b configured to:
- receive the first images I from the display 3;
- process the first images I in such a way as to create processed images IE;
- send the processed images IE towards reflecting elements 5.

the optical system 4a,4b comprises at least one lens.

In particular, the optical system 4a can comprise one or more lenses according to the particular functionality of the augmented reality glasses 1 manufactured.

The optical system 4a,4b is configured to receive the first images I from the display 3.

The optical system 4a,4b is configured to process the first images I in such a way as to create processed images IE.

More precisely, the optical system 4a,4b is configured to collimate and enlarge the first images I in such a way as to create processed images IE.

The optical system 4a,4b is further configured to direct the processed images IE away from the glasses lenses 2a, 2b towards the internal zone 51 of the glasses.

In other words, the optical system 4a,4b is configured to direct the processed images IE in a direction towards the internal zone 51 of the glasses, away from a plane D-D comprising the longitudinal extent of the glasses lens 2a,2b.

According to the invention, the frame 15 has associated with it second reflecting elements 5, in particular comprising mirrors.

Preferably, the reflecting elements 5 are set in the frame 15.

According to the invention, the reflecting elements 5 are configured to receive the processed images IE and reflect them at a first predefined angle α (FIG. 2) towards the glasses lens 2a, 2b.

In particular, these reflection means 5 are configured to project the processed image IE towards the glasses lens 2a, 2b.

Yet more particularly, the reflected images generate a projected image IP on the glasses lens 2a,2b.

In other words, the second reflecting elements 5 comprise a mirror 5 configured to receive said processed images IE and reflect them at a first predefined angle α towards the glasses lens 2a, 2b, in such a way as to project said processed image IE onto the glasses lens 2a, 2b.

In both embodiments, the lens 2a, 2b is configured to reflect the image IE, IE1 originating from the reflection means 3, 5 with an image IP projected towards the internal zone 51 of the glasses, in particular along the visual axis A-A of the eyes of the user who is wearing said glasses.

In other words, the lens 2a, 2b is configured to reflect the second images IE1 or the processed images IE with an image IP projected towards an internal zone 51 of the glasses corresponding to an eye position zone of the user who is wearing the glasses, the projected image IP being projected along the visual axis (A-A) of the eyes of the user who is wearing the glasses in a configuration for use of the glasses.

The optical system 4a, 4b for projecting the images originating from the display can preferably be made up of:
- one or more spherical or aspherical glass lenses, also made of several materials with different refraction indices; the lenses may or may not be treated with a suitable A/R (anti-reflective) coating;
- one or more plastic lenses, also made of several materials with different refraction indices; the lenses may or may not be treated with a suitable A/R (anti-reflective) coating,
- reflecting elements for sending the image back towards the lens of the glasses and which may or may not be present.

The materials with different refraction indices will be adopted to minimise the chromatic aberrations of the system for projection into the user's eye, whilst the A/R coatings will serve to minimise the internal reflections of the system and maximise the projected luminous intensity.

In both embodiments of the invention, the glasses 1 will comprise lenses 2a, 2b, which can be produced with various constructive technologies that will deliver optical information coming from the display 3 or from the optical system 4a,4b or reflecting elements 5 into the surgeon's eye and simultaneously enable him or her to view the external scene.

The function of the lens of the glasses is to reflect the image coming from the display 3 into the surgeon's eye, i.e. the surgeon will be able to observe the external scene and simultaneously a virtual scene coming from the display 3 of the glasses will be superimposed. The result for the surgeon will be a semi-transparent image coming from the display 3 which is suspended within the visual field.

In other words, the function of the lens of the glasses is to convey the image coming from the display 3 towards the visual field of the surgeon, who will be able to observe the real external scene and simultaneously the virtual one superimposed on the latter and coming from the display 3 of the glasses. The result for the surgeon will be a view of the image coming from the display 3 superimposed on that of the surrounding environment, with the creation of a visual experience in which the image coming from the display will be perceived as suspended, in transparency, in the space in front of the surgeon.

In one embodiment, the lens 2a, 2b is realised as a semi-reflective mirror.

The achieved technical effect is that the semi-reflective mirror inside the lens of the glasses serves both to reflect the image coming from the display and to transmit the images coming from outside like a normal pair of glasses.

Advantageously, according to the invention, this type of lens will have a more or less marked absorption of the light coming from outside, somewhat like an only slightly dark sunglass lens.

Advantageously, according to the invention, this configuration will be dedicated to applications in which the external lighting is such as to enable the surgeon to have a good view of the external scene despite the absorption of the semi-reflective mirror inside lens of the glasses.

The technical effect achieved is to ensure a chromaticity such as not to obscure the lens.

In one embodiment of the invention, the lens 2a, 2b is realised as a lens of construction.

In one embodiment of the invention, the lens 2a, 2b is realised as a holographic component distributed over the whole lens.

Preferably, the lens 2a, 2b is realised as a monochromatic holographic component with non-linear optical properties that enable the image coming from the display to be reflected at a certain angle on an ocular axis or at a different angle if the image is required in a different position.

The technical effect of this technological solution is to enable the user to display the images coming from the display and simultaneously observe the images of the outside reality considering a good degree of transparency of the lens of the glasses, almost completely clear. This mode is dedicated to the transmission of texts or monochromatic images to the surgeon.

Alternatively, the lens 2a, 2b is realised as a polychromatic holographic component with non-linear optical properties which enable the image coming from the display to be reflected at a certain angle on an ocular axis or at a different angle if the image is required in a different position.

The technical effect of this technological solution is that it enables the user to display the images coming from the display and simultaneously to observe the images of the outside reality considering a good degree of transparency of the lens of the glasses, almost completely clear.

Unlike the previous monochromatic application, this application is dedicated to the transmission of colour images to the surgeon, where the light conditions impose a high transparency of the lens of the glasses.

In an alternative embodiment, the lens is realised as a coating of nanostructured material, preferably based on surface plasmonic processes.

As already mentioned, the glasses 1, according to the invention, are particularly well suited to being included in an augmented reality system for medical applications.

More specifically, the present invention relates to the biomedical application of glasses (wearable display) capable of superimposing on the visual field of a user, preferably a surgeon, images coming from a display (display or micro display), preferably integrated into the glasses, and in connection with external medical devices, wherein the images are digital or of the CGI (Computer Generated Image) type.

Such images are preferably generated by devices for biomedical applications and are sent to the display so that from the latter, as described below, they can be re-directed towards the visual field of the user. The information contained in the images and coming from the micro display is preferably health related and regards, for example, data, information and static or dynamic images of medical relevance, for example the patient's data, test results, vital parameters of the patient or other information from the instruments used, X-ray images, X-ray images for navigation and virtual images.

The technical effect is represented by the possibility of receiving images or text information projected onto the visual field of the glasses which will enable the physician or surgeon not to lose sight of the patient and/or surgical field during any therapeutic procedure or operating step. This will increase the speed and precision of the medical/surgical act because it will not be necessary to shift attention from the patient to other sources of information such as the instrument monitor, the terminal displaying X-ray images or any other external computerised source of patient clinical data.

The augmented reality system for medical applications on a user, according to the invention comprises the augmented reality glasses 1 described.

The system further comprises biomedical instrumentation 100 configured to acquire biomedical and/or therapeutic and/or diagnostic data and to generate first data D1 representative of operational parameters OP_S associated with the user.

The system further comprises a transmitting means 101 configured to transmit the first data D1 to the glasses 1, in particular to the receiving module 102 of the first processing unit 10.

Preferably, the transmitting means 101 comprises a data connector.

Alternatively, or in addition, the transmitting means 101 comprises a wireless transmitter.

The glasses 1 according to the invention comprise the first processing unit 10.

The first processing unit 10 according to the invention comprises a receiving module 102 configured to receive the first data D1 representative of operational parameters OP_S.

Preferably, the operational parameters OP_S comprise one or more among diagnostic parameters, clinical parameters in text and/or graphic form, vital parameters, technical parameters related to instrument settings, biological parameters, clinical information concerning the patient and similar data.

The first processing unit 10 is configured to process data D1 input to the glasses 1 so as to generate corresponding first images I on the display 3.

Advantageously, according to the invention, the augmented reality system further comprises a second processing unit 80.

In general, it should be noted that in the present context and in the subsequent claims, the processing unit 80 is presented as being divided into distinct functional modules (storage modules and operative modules) for the sole purpose of describing clearly and completely the functionalities of the processing unit 80 itself.

In reality this processing unit 80 can consist of a single electronic device (or card), appropriately programmed to perform the functionalities described, and the different modules can correspond to hardware entities and/or routine software forming part of the programmed device.

The processing unit 80 can also make use of one or more processors for executing the instructions contained in the storage modules.

In one embodiment of the invention, the processing unit 80 is included in the glasses 1, in particular in the first processing unit 10.

In an alternative embodiment, the processing unit 80 is external to the glasses 1 and in a data connection therewith.

The processing unit 80 comprises a receiving module 81 configured to receive the first data D1 representative of operational parameters OP_S.

In other words, the processing unit 80 receives all the information relating to the user being monitored and determines the best use thereof based on the instructions given by medical/health care personnel.

The processing unit 80 comprises a display module 82 configured to display the first data D1 on the display 3 in such a way that they are projected onto the centre of the lens 2a, 2b.

In other words, when the data are retrieved from the biomedical instrumentation 100, they are "presented" at the centre of the lens 2a, 2b so that the user can see them and decide what use to make of them.

The processing unit 80 comprises a command module 83 configured to receive second data D2 representative of a position on the lens 2a, 2b where the first data D1 must be displayed.

The processing unit 80 is associated, in particular in a data connection, with a command unit 90, 91 configured to generate the second data D2.

In one embodiment of the invention, the command unit 90 comprises a voice command receiver 90.

In other words, after the data are "presented" at the centre of the lens 2a, 2b, the doctor or health care personnel who are using the system emit a voice command representative of the second data D2 for positioning the data D1 on the lens 2a, 2b; the command can be of the type "move to the right/left, so that the data will be destined to an area of the lens that is not at the centre of the observed scene, or else it can be of the type "move forward/move back" so that the data will be destined to an area that is nearer to or farther from the centre of the observed scene, or else it can be "lock" to fix the position occupied by the data.

In other words, the image of the first data D1 can be
- at the centre of the visual field, displayed on the operating field;
- at the centre of the visual field, displayed nearer or farther away relative to the operating field;
- in a peripheral position relative to the centre of the visual field, in any point that is convenient for the surgeon's vision but does not visually interfere with the area operated on.

In one embodiment of the invention, the command unit 91 comprises a pointer means, in particular a mouse 91.

In other words, after the data are "presented" at the centre of the lens 2a, 2b, the doctor or health care personnel who are using the system will move the mouse representative of the second data D2 for positioning the data D1 on the lens 2a, 2b in such a way that the data will be destined to an area of the lens that is not at the centre of the observed scene.

The processing unit comprises a positioning module 84 configured to project the first data D1 on the lens 2a, 2b in a given position based on the second data D2 received; in other words, the positioning module 84 converts the command received from the units 90 or 91 for the processing unit.

The system of the invention, as already mentioned, comprises biomedical instrumentation 100, in particular one or more among:
PACS systems (picture archiving and communication system);
surgical navigators;
endoscopes;
integrated operating room systems that acquire the patient's vital parameters and the surgical instrument settings;
integrated systems for collecting the patient's clinical data and vital parameters for use outside the operating room;
surgical simulators for educational activities.

PACS systems are hardware and software systems dedicated to archiving, transmission, display and printing of digital diagnostic images.

The innovation tied to the system of the invention derives from the possibility of using the data generated by the PACS, as first data D1 representing operating parameters OP_S, for a display of digital diagnostic images in any point of the visual field where the surgeon wishes to receive them, also so as to be able to have them available during every therapeutic procedure or operating step.

The surgical navigator is a device capable of correlating in space the patient, the images thereof originating from a computed tomography (CT) or magnetic resonance (MR) scan and the instrument the surgeon is using, so that if the surgeon's instrument touches the patient in a given point, the navigator will show where that point is located on the CT or MR image displayed on its screen. It is possible to superimpose on the X-ray images shown by the navigator a processed version of the same images which represents the surgical plan to be carried out during the surgery (for example, if the surgery entails moving a bone segment, the navigator will show the patient's CT scan prior to surgery and superimpose the "virtual" CT of the patient as it should be after the surgery: having the X-ray, plan and current real position of the instrument on the screen, the surgeon can check whether that bone segment has been moved in space exactly where planned virtually).

The navigator consists of a central computer equipped with an infrared camera or an electromagnetic field generator and several detectors communicating with it: one detector on the patient and one on the surgeon's instrument. The use of a navigator involves starting the surgery by positioning the detector on the patient and "registering" the latter, that is, a process that culminates with the spatial correspondence between real anatomy, X-ray images (native CT scan and processed CT scan) and instruments. The innovation tied to the system of the invention derives from the possibility of using the visual information described above as first data D1 representative of operational parameters OP_S OP_S visible through the glasses 1 of the invention.

In the case concerned, graphic information normally displayed on the screen of the navigator is displayed in the visual field, i.e. projected onto the lens 2a, 2b of the glasses 1 worn by the surgeon, thus enabling the latter not to divert their visual attention from the operating field and hence from the anatomical structure being acted on and which is the object of the navigation. This is particularly important because every surgical act (for example the repositioning of bone segments) requires constant visual monitoring and the standard use of the navigator obliges surgeons to divert their gaze for the time necessary to check the images of the navigator and simultaneously hold the navigated instrument and in some cases the anatomical part operated on as well. As a result, part of the increase in precision imparted by the use of the navigator is undermined by the interference of the lack of direct visual monitoring or the entire procedure is made particularly difficult for the surgeon.

With the system of the invention, as previously described, the image coming from the navigator can be projected in any point of the visual field during surgery, enabling, for example, the following options, based on the most comfortable solution for the operator:

Semi-transparent image (or non-transparent image during non-operative steps) at the centre of the visual field, displayed over the operating field;
Semi-transparent or non-transparent image (or non-transparent image during non-operative steps) at the centre of the visual field, displayed nearer or farther away relative to the operating field;
Semi-transparent or non-transparent image in a peripheral position relative to the centre of the visual field, in any point that is convenient for the surgeon's vision but does not visually interfere with the area operated on.

An endoscope is a diagnostic and surgical device consisting of a camera connected to a rigid or flexible tube, at the end of which there is an optical system capable of transmitting the images coming from internal anatomical cavities of the patient and displaying them on a screen; alternatively, the camera can be miniaturized and mounted directly on the end of the tube.

This device is an aid to the clinician both at the stage of diagnosis of pathologies of the natural internal cavities of the patient for example the nose, digestive tube, tracheal-bronchial shaft . . . ) and at the stage of treatment of the same or of pathologies reached through the creation of new cavities (peritoneal cavity insufflated with air, mini-invasive routes of access to deep structures).

The innovation tied to the system of the invention derives from the possibility of viewing on the lens 2a, 2b, at any point of the surgeon's visual field, all or a selected part of this information, as first data D1 representative of operational parameters OP_S, the image coming from the endoscope, so that operators do not have to turn their gaze to a monitor far from the operating field, but can rather maintain their attention, as desired, on the way in which their instrument is maneuvered, and hence on the use of their hands coupled with the internal surgical activity.

With the system of the invention, the image coming from the endoscope can be projected in any part of the visual field during surgery, enabling, for example, the following options, based on the most comfortable solution for the operator:

Semi-transparent or non-transparent image at the centre of the visual field, displayed over the operating field;
Semi-transparent or non-transparent image at the centre of the visual field, displayed nearer or farther away relative to the operating field;
Semi-transparent or non-transparent image in a peripheral position relative to the centre of the visual field, in any point that is convenient for the surgeon's vision but does not visually interfere with the area operated on.

An integrated operating room system makes it possible to collect information such as the vital parameters of the patient (for example: pressure values, heart rate, etc.) and the operation of all instruments and devices present in an operating room (for example: anaesthesiologist breathing apparatus, electric knives, laser knives, burrs and other cutting instruments, bone modelling and synthesis, operating times . . . ).

The innovation tied to the system of the invention derives from the possibility of viewing on the lens 2a, 2b, at any point of the surgeon's visual field, all or a selected part of this information, as first data representative of operational parameters OP_S.

At this point the surgeon can access two modes of analysis, both of them important:

observation of how the instruments they are using are acting on the patient, for example, in the case of a surgical drill, whether the rotation is too slow or too fast and therefore whether the action of the instrument being used is excessive;
knowledge of the instrument setting parameters without having to ask operating room staff or diverting their gaze and thus attention from the area being operated on, for example to view them on the monitor.

An integrated system for collecting clinical data and/or vital parameters makes it possible to display on request, as first data D1 representative of operational parameters OP_S, the patient's personal or objective clinical information (including results of laboratory tests or X-rays), or else vital parameters (static or dynamic) acquired by specific instruments (for example: ECG tracing, pressure values, ventilating values or any other data originating from an anaesthesia breathing apparatus or intensive monitoring, etc.). The use in departments or on the field (for example: ambulance or emergency services) is similar to that described in the paragraph relating to operating rooms.

In this case as well, the innovation tied to the system of the invention derives from the possibility of displaying, in any part of the surgeon's visual field, all or a selected part of this information, without the need to look away from the patient during therapeutic procedures or assistance, also in cases of emergency/urgency.

Use can also be extended to information for locating the ill person in the case of ambulance services (for example the address and road directions for the ambulance driver or other operators of the team projected on the same device that will then serve as a collector and device for displaying clinical information, without the need to have to change glasses between one phase and another).

In the case of surgical simulators for educational activity, the innovation tied to the system of the invention derives from the possibility of displaying, in any point of the visual field, as first data D1 representative of operational parameters OP_S, anatomical plates, anatomical and/or functional diagrams, surgical diagrams or text indications during a teaching procedure such as dissection of an animal or human cadaver.

Based on what has been described, it can be understood that the glasses and system of the invention are a first step toward achieving integration in an augmented reality system in the medical-surgical field which enables virtual reconstructions of the anatomy of the patients to be displayed directly over the latter and the surgical plan, where present, combines the advantages of the innovative glasses with the possibility of eliminating any other mediation between the virtual data and real data.

In surgery and anatomy, augmented reality enriches the concept of correlation between real and virtual anatomy with the possibility of projecting directly over the patient radiographic information in the correct topographic position.

The innovation tied to the specific use of the augmented reality glasses is the possibility of seeing the patient and/or the area operated on in transparency through the lens of the glasses and simultaneously view the virtual images superimposed over the patient which can represent surface maps or internal anatomical or pathological structures, surgical plans or the position of the surgical instruments in the case of so-called closed operating techniques (the instruments are not visible to the direct observation of the surgeon and are presently displayed by means of endoscopic or radiological techniques), thus achieving an integration between real and virtual images.

The invention claimed is:

1. Augmented reality glasses (1) configured to be worn by a user, wherein said glasses (1) comprise a frame (15) that supports a glasses lens (2a, 2b), wherein said frame (15) comprises:
    a) an RGB lighting system comprising:
        1) at least one RGB-emitting device (16a, 16b, 16c) configured to emit a light beam (B1, B2, B3);
        2) at least a first optical system (17a, 17b, 17c) configured to collimate at least partially said beam (B1, B2, B3) received from the at least one RGB-emitting device (16a, 16b, 16c) into a collimated beam (B1c, B2c, B3c);
    b) a display (3) configured to
        1) be illuminated by said lighting system (16) by means of at least said collimated beam (B1c, B21c, B31c);
        2) receive first images (I) from a first processing unit (10);
        3) emit said first images (I) as second images (IE1) towards said glasses lens (2a, 2b);
    c) wherein the lens (2a, 2b) is configured to reflect the second images (IE1) coming from reflecting means (3) as images (IP) projected towards an internal zone (51) of the glasses corresponding to an eye position zone of said user who is wearing said glasses in a configuration for use of the glasses;
    wherein said lighting system (16) comprises at least a second optical systems (18a, 18b, 18c) configured to filter at least one of said collimated light beams (B1c, B2c, B3c) in at least one of predetermined frequencies (f1, f2, f3), determining at least one of three sub-beams (B11c, B21c, B31c) and said display (3) is configured to be illuminated k y said lighting system (16) by means of at least one of said sub-beams (B11c, B21c, B31c).

2. The glasses (1) according to claim 1, wherein said RGB lighting system (16) is one system among the following:
    a) an RGB LED lighting system;
    b) an RGB laser diode system;
    c) an RGB white LED system.

3. The glasses (1) according to claim 2, wherein said frame (15) comprises an optical system (4a,4b) configured to:
    a) receive said first images (I) from said display (3);
    b) process said images so as to create processed images (IE);
    c) send said processed images (IE) towards reflecting elements (5) or towards said lens (2a,2b).

4. The glasses (1) according to claim 3, wherein said reflecting elements (5) are configured to receive said processed images (IE) and reflect them at a first predefined angle (a) towards said glasses lens (2a, 2b), so as to project said processed image (IE) on said glasses lens (2a, 2b).

5. The glasses (1) according to claim 2, wherein said display (3) comprises a beam splitter (3a) and it is realised as a reflecting element.

6. The glasses (1) according to claim 1, wherein said frame (15) comprises an optical system (4a,4b) configured to:
    a) receive said first images (I) from said display (3);
    b) process said images so as to create processed images (IE);
    c) send said processed images (IE) towards reflecting elements (5) or towards said lens (2a,2b).

7. The glasses (1) according to claim 6, wherein said reflecting elements (5) are configured to receive said processed images (IE) and reflect them at a first predefined angle (a) towards said glasses lens (2a, 2b), so as to project said processed image (IE) on said glasses lens (2a, 2b).

8. The glasses (1) according to claim 1, wherein said display (3) comprises a beam splitter (3a) and it is realised as a reflecting element.

9. The glasses (1) according to claim 1, comprising two dichroic filters (19) which receive the light beams coming out of the second optical systems (18a, 18b, 18c).

10. The glasses (1) according to claim 1, wherein said lens (2a, 2b) is configured to reflect said second images (IE1) or said processed images (IE) with an image (IP) projected towards an internal zone (51) of the glasses corresponding to an eye position zone of said user who is wearing said glasses, said projected image (IP) being projected along the visual axis (A-A) of the eyes of the user who is wearing said glasses in a configuration for use of the glasses.

11. The glasses (1) according to claim 1, wherein said lens (2, 2b) is realised as a semi-reflective mirror.

12. The glasses (1) according to claim 1, wherein said lens (2a, 2b) is realised as a holographic component.

13. The glasses (1) according to claim 12, wherein said holographic component is monochromatic.

14. The glasses (1) according to claim 12, wherein said holographic component is polychromatic.

15. The glasses according to claim 1, wherein said lens (2a, 2b) is made of nanostructured material and is based on surface plasmonic processes.

16. An augmented reality system for medical applications on a user, wherein the system comprises:
   a) augmented reality glasses (1) according to claim 1;
   b) biomedical instrumentation (100) configured to detect biomedical and/or therapeutic and/or diagnostic data of a user and to generate first data (D1) representative of operational parameters (OP_S) associated with said user (S);
   c) transmitting means (101) configured to transmit said first data (D1) to said glasses (1);
   d) wherein said glasses (1) comprise a first processing unit (10) equipped with a receiving module (102) configured to receive said first data (D1) comprising said operational parameters (OP_S) associated with said user.

17. The augmented reality system according to claim 16, wherein said operational parameters (OP_S) comprise one or more among diagnostic parameters, clinical parameters in text or graphic form, vital parameters, technical parameters related to instrument settings, biological parameters, clinical information concerning the patient and similar data.

18. The augmented reality system according to claim 16, further comprising a second processing unit (80) comprising:
   a) a receiving module (81) configured to receive said first data (D1) representative of operational parameters (OP_S);
   b) a display module (82) configured to display said first data (D1) on said display (3) in such a manner that the data are projected at the centre of the lens (2a, 2b);
   c) a command module (83) configured to receive second data (D2) representative of a position on said lens (2a, 2b) where said first data (D1) must be displayed;
   d) a positioning module (84) configured to project said first data (D1) on said lens in a given position based on said received second data (D2).

19. The system according to claim 18, wherein said first processing unit (10) comprises said second processing unit (80).

20. The augmented reality system according to claim 16, comprising a command unit (90, 91) associated with said processing unit (80), wherein said command unit is configured to generate said second data (D2) representative of a position on said lens (2a, 2b) where said first data (D1) must be displayed.

21. The augmented reality system according to claim 20, wherein said command unit (90) comprises a voice command receiver (90).

22. The augmented reality system according to claim 20, wherein said command unit (91) comprises a mouse (91).

23. The augmented reality system according to claim 16, wherein said biomedical instrumentation (100) comprises one or more among:
   a) PACS systems (picture archiving and communication system);
   b) surgical navigators;
   c) endoscopes;
   d) integrated operating room systems that collect the patient's vital parameters and the surgical instrument settings;
   e) integrated systems for collecting the patient's clinical data and vital parameters for use outside the operating room;
   f) surgical simulators for educational activities.

24. The augmented reality system according to claim 16, wherein said transmitting means (101) is configured to transmit said first data (D1) to said glasses (1), particularly to the receiving module (102) of the first processing unit (10), comprises a data connector.

25. The augmented reality system according to claim 16, wherein said transmitting means (101) configured to transmit said first data (D1) to said glasses (1), particularly to the receiving module (102) of the first processing unit (10), comprises a wireless transmitter.

* * * * *